(12) United States Patent
Takahashi et al.

(10) Patent No.: US 7,550,436 B2
(45) Date of Patent: Jun. 23, 2009

(54) COMPOSITIONS CONTAINING PEPTIDE AND ELECTROLYTE EXCRETION PROMOTER AND FOODS CONTAINING THE SAME

(75) Inventors: Ryuji Takahashi, Takaoka (JP); Satoshi Yomoda, Takaoka (JP)

(73) Assignee: Kracie Pharma, Ltd., Tokyo-To (JP)

( * ) Notice: Subject to any disclaimer, the term of this patent is extended or adjusted under 35 U.S.C. 154(b) by 887 days.

(21) Appl. No.: 10/258,420

(22) PCT Filed: May 8, 2001

(86) PCT No.: PCT/JP01/03827

§ 371 (c)(1),
(2), (4) Date: Oct. 22, 2002

(87) PCT Pub. No.: WO01/84948

PCT Pub. Date: Nov. 15, 2001

(65) Prior Publication Data

US 2003/0144179 A1    Jul. 31, 2003

(30) Foreign Application Priority Data

May 11, 2000    (JP) ............................... 2000-138373

(51) Int. Cl.
*A61K 38/10*    (2006.01)
*G01N 33/53*    (2006.01)
(52) U.S. Cl. .................. 514/14; 530/327; 435/7.71
(58) Field of Classification Search ............... None
See application file for complete search history.

(56) References Cited

U.S. PATENT DOCUMENTS

| | | | | |
|---|---|---|---|---|
| 4,179,433 A | * | 12/1979 | Kisfaludy et al. | 530/316 |
| 4,738,850 A | * | 4/1988 | Thakur et al. | 424/468 |
| 5,618,699 A | * | 4/1997 | Hamamoto et al. | 435/69.7 |
| 6,136,349 A | * | 10/2000 | Karppanen et al. | 426/2 |

FOREIGN PATENT DOCUMENTS

| | | | |
|---|---|---|---|
| EP | 0 464 299 | | 1/1992 |
| JP | 58-109425 | | 6/1983 |
| JP | 59-044324 | | 3/1984 |
| JP | 61-036226 | | 2/1986 |
| JP | 61-036227 | | 2/1986 |
| JP | 62-270533 | | 11/1987 |
| JP | 64-009938 | | 1/1989 |
| JP | 01-187067 | | 7/1989 |
| JP | 02-167052 | | 6/1990 |
| JP | 02-268649 | | 11/1990 |
| JP | 04-074124 | | 3/1992 |
| JP | 404341193 A | * | 11/1992 |
| JP | 06-056674 | * | 3/1994 |
| JP | 06-197727 | | 7/1994 |
| JP | 06-211690 | | 8/1994 |
| JP | 09-249694 | | 9/1997 |
| JP | 11-240841 | | 9/1999 |
| JP | 11-263733 | * | 9/1999 |

OTHER PUBLICATIONS

Kawashima, 1985, Chem Pharm. Bull., 33, 2107-2113.*
Okuda (Ed.) *Chitosan-to-Chitosan Kiso-to-Yakuri (Basis of Pharmacology of Chitin and Chitosan*, 3rd Edition, pp. 28-35 (1997).
Kato et al. "Antihypertensive effect of chitosan in rats and humans". *Journal of Traditional Medicines*, vol. 11, pp. 198-205 (1994).

* cited by examiner

*Primary Examiner*—Andrew D Kosar
*Assistant Examiner*—Satyanarayana R Gudibande
(74) *Attorney, Agent, or Firm*—Hamre, Schumann, Mueller & Larson, P.C.

(57) ABSTRACT

A composition containing a peptide and an electrolyte excretion promoter, which comprises a peptide or a peptide mixture which is obtained by lysing a food-origin protein with a protease and has an activity of inhibiting angiotensin converting enzyme, and one or more electrolyte excretion promoters selected from chitosan, alginic acid or a salt thereof, and further relates to a food containing the same. Said composition has excellent inhibitory activity to rise of blood pressure by synergistic effects of both components.

6 Claims, 1 Drawing Sheet

```
                              SEQUENCE LISTING

<160> NUMBER OF SEQ ID NOS: 3

<210> SEQ ID NO 1
<211> LENGTH: 12
<212> TYPE: PRT
<213> ORGANISM: Bos taurus

<400> SEQUENCE: 1

Phe Phe Val Ala Pro Phe Pro Glu Val Phe Gly Lys
1               5                   10

<210> SEQ ID NO 2
<211> LENGTH: 7
<212> TYPE: PRT
<213> ORGANISM: Bos taurus

<400> SEQUENCE: 2

Ala Val Pro Tyr Pro Gln Arg
1               5

<210> SEQ ID NO 3
<211> LENGTH: 6
<212> TYPE: PRT
<213> ORGANISM: Bos taurus

<400> SEQUENCE: 3

Thr Thr Met Pro Leu Trp
1               5
```

US 7,550,436 B2

COMPOSITIONS CONTAINING PEPTIDE AND ELECTROLYTE EXCRETION PROMOTER AND FOODS CONTAINING THE SAME

TECHNICAL FIELD

The present invention relates to a composition containing a peptide and an electrolyte excretion promoter and a food containing the same. More particularly, it relates to a composition containing a peptide and an electrolyte excretion promoter, which comprises a peptide or a peptide mixture which is obtained by lysing a food-origin protein with a protease and has an activity of inhibiting angiotensin converting enzyme, and one or more electrolyte excretion promoters selected from chitosan, alginic acid and a salt thereof, and further relates to a food containing the same.

BACKGROUND ART

Movement for healthy life has recently positively been taken in Japan aiming at improvement of lifestyle, reduction of risk factors, or reduction of diseases, and awareness for healthy life has been raised globally.

Particularly, with respect to circulatory diseases, it is assumed that for example, when the blood pressure of people of Japan is lowered in the degree of 2 mmHg in average, fatalities due to cerebral stroke will be reduced about 10,000 persons, and lowering of activities of daily living (ADL) of 3,500 persons can be prevented.

From the viewpoint of the above circumstance, various kinds of foods have been developed, those containing a food protein-origin peptide which has hypotensive activity.

For example, it has been reported that a peptide or a peptide mixture obtained by lysing cow's milk-origin casein with trypsin or pepsin include one or more peptides having a sequence of (a) Phe-Phe-Val-Ala-Pro-Phe-Pro-Glu-Val-Phe-Gly-Lys (Seq. ID No. 1) (hereinafter, occasionally referred to as "C12"), (b) Ala-Val-Pro-Tyr-Pro-Gln-Arg (Seq. ID No. 2) (hereinafter, occasionally referred to as "Cβ7"), and (c) Thr-Thr-Met-Pro-Leu-Trp (Seq. ID No. 3) (hereinafter, occasionally referred to as "C6"), or an acid addition salt thereof, which have an inhibitory activity to angiotensin converting enzyme (hereinafter, abbreviated as "ACE") (cf. JP-B -60-23085, JP-B-61-51562, and JP-B-61-51564); that a crude composition comprising mainly the above-mentioned peptide or peptide mixture (such a crude composition is also included in the peptide of the present invention) has ACE inhibitory activity likewise (cf. JP-B-5-21092). It has been expected that the peptide or peptide mixture will be useful as a material not only for the treatment of hypertension but also for the prevention of hypertension (cf. JP-B-4-58947, JP-A-64-9938 and JP-A-1-187067). Moreover, it has been known that a pepsin-lytic product of cow's milk casein has sedative activity (JP-B-5-81220); that a trypsin-lytic product of cow's milk-origin casein has hyperlipidemia inhibitory activity (cf. JP-A-6-211690) or has an activity of prevention of cerebral stroke (cf. U.S. Pat. No. 5,703,212).

It is also known that the foods-origin peptide or peptide mixture as mentioned above have usually strong bitter taste and/or astringent taste.

It has been tried to reduce or modify such bitter taste and/or astringent taste of the foods-origin peptide or peptide mixture by using various kinds of additives. For example, JP-A-9-249694 discloses an aqueous solution suitable for oral administration which comprises (a) a peptide or peptide mixture having bitter taste and/or astringent taste, (b) a sugar alcohol, (c) an acidic flavor, and (d) a plum type flavor.

On the other hand, it has been know that as to the electrolyte excretion promoter to be used in the present invention, chitosan has an activity of binding to chlorine contained in foods to excrete it out of the body, and alginic acid or a salt thereof has an activity of binding to sodium contained in foods to excrete it out of the body, and hence, these substances are used as a material for healthy foods for the purpose of low-salt diet.

Research and development of chitosan (β-1,4'-poly-D-glucosamine) have been done in various fields and is has been used in various kinds of products. Chitosan is produced by partially or completely de-acetylating a polysaccharide chitin (β-1,4'-poly-N-acetyl-D -glucosamine) which composes shell of shellfish or cuttlebone, and various products having various molecular weights are commercially available. Alginic acid is a natural polysaccharide which is contained particularly in brown color weeds such as sea tangle and wakame seaweed.

In has been known that chitosan has also an hypotensive activity. For example, JP-A-6-56674 discloses a food additive comprising chitosan as an active ingredient which is useful for promoting excretion of chlorine in foods and a food additive comprising chitosan as an active ingredient which is useful for hypotension. However, the hypotensive activity of the product is merely effective for inhibiting rise of blood pressure due to increase of chlorine in serum after taking high salt diet, but it is not expected to reduce the blood pressure after taking a normal food in such a degree as in the case of taking of high salt diet. (cf. Chitin-to-Chitosan Kiso-to-Yakuri (Basis and Pharmacology of Chitin and Chitosan), 3rd Edition, pp. 28-35, edited by Takumichi OKUDA, Yakkyoku Shinbunsha, 1997).

Moreover, alginic acid has also been known as one of the components of sea tangle, of which hypotensive activity has been known from a long time ago. That is, it is considered that the hypotensive activity of sea tangle will be exhibited by binding alginic acid to sodium contained in the ingested foods and then excreting it out of the body. Thus, the hypotensive activity will be exhibited owing to desalt effect and thereby a salt-sensitive hypertension will secondarily be prevented.

Any of the patent publications and literatures as mentioned above do never disclose a composition comprising a peptide or a peptide mixture which is obtained by lysing a food-origin protein with a protease and has an inhibitory activity to ACE and an electrolyte excretion promoter.

DISCLOSURE OF INVENTION

An object of the invention is to provide a composition comprising a peptide or a peptide mixture which is obtained by lysing a food-origin protein with a protease and has an inhibitory activity to ACE and one or more electrolyte excretion promoters selected from chitosan and alginic acid or a salt thereof, which has excellent hypertension inhibitory activity and is useful for improvement of lifestyle, reduction of risk factors, and reduction of diseases, and also to provide a food containing the same.

According to the research by the present inventors, it has been found that by combining a peptide or a peptide mixture which is obtained by lysing a food-origin protein with a protease and has an inhibitory activity to ACE with one or more electrolyte excretion promoters selected from chitosan and alginic acid or a salt thereof, they exhibit excellent synergistic effects and show far superior hypertension inhibitory activity in comparison with the activities exhibited by each component alone, and based on the new findings, the present invention has been completed.

BEST MODE FOR CARRYING OUT THE INVENTION

Figure 1:
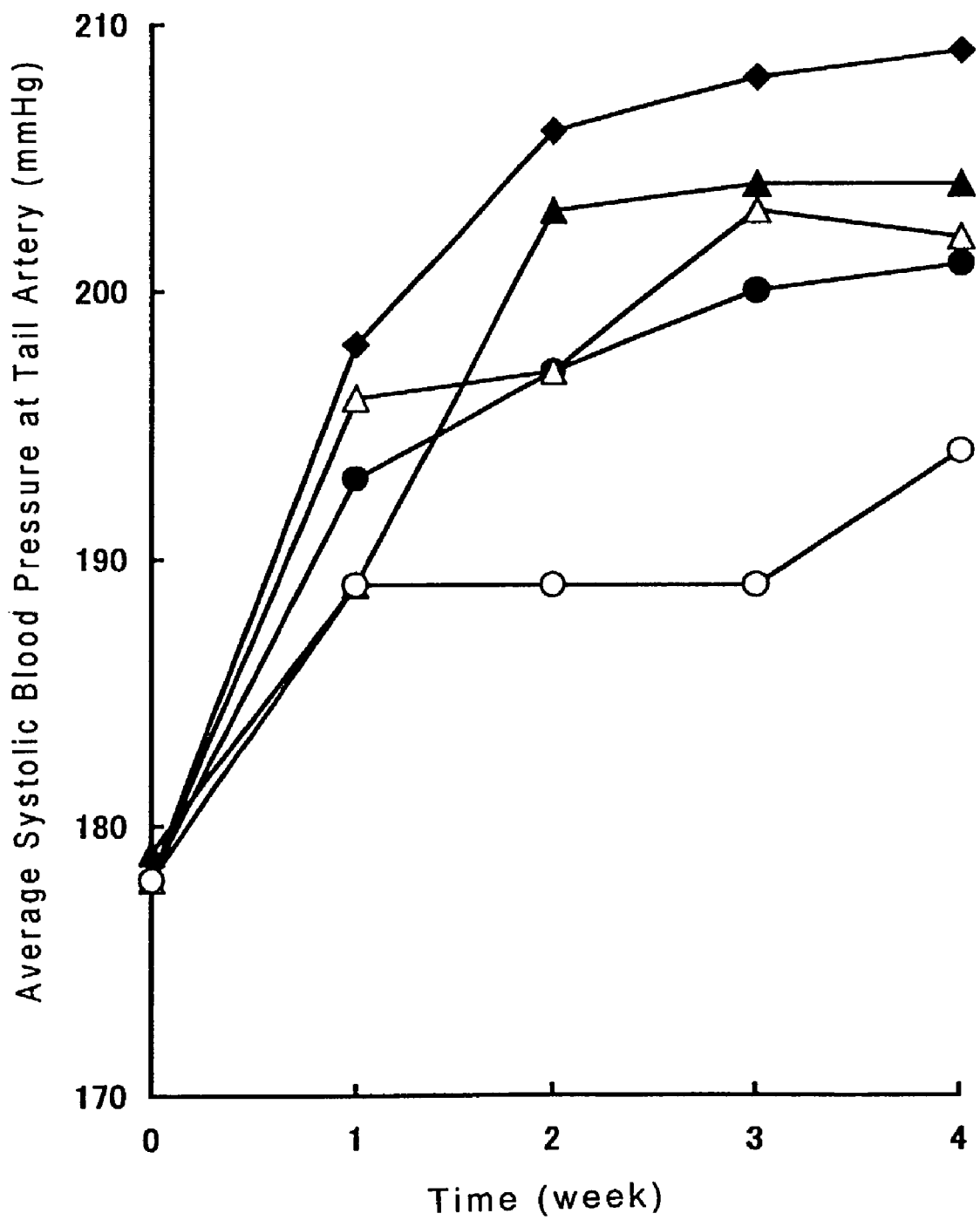
FIG. 1 is a graph showing the change in average of systolic blood pressure per each week at a tail artery in spontaneous hypertensive rats (SHR), wherein the symbol ○ means the case of ingestion of Sample "a" for administration to rats, the symbol Δ means the case of ingestion of Sample "b" for administration to rats, the symbol ● means the case of ingestion of Comparative Sample "c" for administration to rats, the symbol ▲ means the case of ingestion of Comparative Sample "d" for administration to rats, the symbol ♦ means the case of ingestion of Control Sample "e" for administration to rats.

The peptide or peptide mixture used in the present invention includes any product obtained by lysing a food-origin protein with a protease which has an inhibitory activity to ACE and is not limited to specific product, but preferably a low molecular weight product (e.g. a peptide fraction having a molecular weight of not more than 5,000, preferably a peptide fraction having a molecular weight of not more 3,000), which is obtained by lysing a casein with a protease: trypsin followed by partial purification of the proteolytic product.

Such low molecular weight peptides are prepared in the following manner.

Caseins which have widely been used as a food additive (for example, cow's milk-origin casein, acid casein, casein salts, rennet-casein, etc.) are subjected to hydrolysis with a commercially available trypsin, preferably highly pure trypsin. The hydrolysis of casein with trypsin is usually carried out by adjusting the casein aqueous solution to neutral or alkaline region and allowing the aqueous solution (having preferably a protein concentration of about 10 % by weight) to reaction at about pH 7.5 for 2 to 5 hours. The hydrolysis reaction can be ceased by heating at 121° C. for 10 minutes to deactivate the enzyme. After completion of the reaction, the insoluble fraction is removed by centrifugation or filtration, and the supernatant or filtrate is fractionated with a ultrafiltration membrane (e.g., SEP 1013, manufactured by Asahi Kasei Corporation; Amikon H10 P3-20, manufactured by Grace Japan; UFP-3-E-9A, manufactured by A/G Technology, etc.) or with gel permeation chromatography (GPC) ligand (e.g., Sephadex G-25, manufactured by Pharmacia; Sephacryl S-100HR, manufactured by Pharmacia; Bio-Gel P-6, manufactured by Bio-Rad Lab.; Toyopearl HW-40, manufactured by Tasoh Corporation, etc.) to separate peptides having a molecular weight of about 3,000 to 5,000.

This low molecular weight peptide fraction comprises peptides having a molecular weight of not more than 5,000, preferably not more than 3,000. Specific examples are one or more of a peptide or a peptide mixture selected from C12, Cβ7 and C6 or an acid addition salt thereof as mentioned above.

Each peptide of the above C12, Cβ7 and C6 or a crude product comprising mainly each of those peptides (hereinafter, referred to as "peptide crude product) are obtained by the methods disclosed in JP-B-60-23085, JP-B-61-51562, JP-B-61-51564, JP-B-5-21092, JP-B-60-23087.

The electrolyte excretion promoter used in the present invention is selected from chitosan and alginic acid or a salt thereof among substances which are able to reduce sodium and chlorine in serum which are a factor inducing rise of blood pressure, said substances being used alone or in a mixture of two or more thereof.

The chitosan used in the present invention may be any product which is produced by partially or completely de-acetylating a chitin obtained from shell of crab, shrimp, etc., cuttlebone, cells of fungi, which is effected by heat-treatment of the chitin with a conc. alkali solution such as a 40-50% aqueous sodium hydroxide solution. Preferred one is a product having a low viscosity as mentioned below in view of the object of the present invention. The preferable chitosans are commercially available, for example Koyo Chitosan FL-80, Koyo Chitosan FM-80, Koyo Chitosan FH-80, Chitosan Oligosaccharide (which are all manufactured by Koyo Chemical Co., Ltd.); Kirin High Molecular Weight Chitosan (manufactured by Kirin Brewery Co., Ltd.); Kimitsu Chitosan LL, Kimitsu Chitosan L, Kimitsu Chitosan M, Kimitsu Chitosan H (which are all manufactured by Kimitsu Chemical Industry Co., Ltd.).

These chitosans may have various viscosities, but preferable chitosan has such an average molecular weight that it shows a viscosity of not more than 100 mPa·s at 20° C. in a 0.5% aqueous solution. More preferable chitosan has such an average molecular weight that it shows a viscosity of not more than 15 mPa·s at 20° C. in a 1% aqueous solution. Preferred example is the above Koyo Chitosan FL-80.

The alginic acid or a salt thereof used in the present invention includes alginic acid and alginates such as sodium alginate, potassium alginate, ammonium alginate which are usually used as a food additive. Commercially available products are, for example, Duck Acid (alginic acid), Duck Algine NSP (sodium alginate), Duck Algine K (potassium alginate), Duck Ammone (ammonium alginate) (which are all manufactured by Kibun Food Chemifa Co., Ltd. ).

The composition containing a peptide and an electrolyte excretion promoter of the present invention may be a mere mixture of a peptide or a peptide mixture of the above-mentioned C12 or Cβ7 and an electrolyte excretion promoter selected from one or more of chitosan and alginic acid or a salt thereof, but it is usually prepared in the form of granules by admixing with conventional excipients for foodstuffs (e.g. crystalline cellulose, sucrose fatty acid esters, white sugar, etc.) and granulating the mixture, for example, by a dry granulation method or a wet granulation method.

Besides, the composition may be prepared in the form of a liquid by dissolving them in a conventional liquid excipient for foodstuffs (e.g. acidifier or sugar alcohol, etc.).

In the composition containing a peptide and an electrolyte excretion promoter of the present invention, the peptide and the electrolyte excretion promoter are contained in various amounts which are dependent on the kinds of the peptides and the electrolyte excretion promoters used, but the peptide is usually contained in an amount of 10 to 1,000 parts by weight, preferably 20 to 500 parts by weight, more preferably 20 to 200 parts by weight, and the electrolyte excretion promoter is contained in an amount of 50 to 5,000 parts by weight, preferably 100 to 4,000 parts by weight, more preferably 200 to 2,000 parts by weight. The ratio of the peptide and the electrolyte excretion promoter is usually in the range of 1 to 500 parts by weight, preferably 2 to 200 parts by weight, more preferably 4 to 100 parts by weight, of the electrolyte excretion promoter per 1 part by weight of the peptide.

The composition of the present invention is used, either in situ or in the form of a food, in such an amount that it exhibits the desired hypotensive activity. That is, in one embodiment, the composition contains the peptide or peptide mixture of 10 mg to 1,000 mg and the electrolyte excretion promoter of 50 mg to 5,000 mg in a single dosage unit.

For example, in case of C12, the peptide or peptide mixture is preferably contained in the composition or in the food in an amount of 50 to 200 mg as a daily dosage in adult. In this case, the composition or food may contain C12 alone as the peptide but preferably contain as a peptide crude product comprising a mixture thereof with other peptide. Moreover, the composition or food contains chitosan and alginic acid in an amount of 50 mg to 500 mg.

The food of the present invention may be used in the granules per se as prepared in the manner as mentioned above and alternatively may be used in the form of a compressed product prepared by compressing them with a tableting machine, or may also be used in the form of a liquid.

The peptide and peptide mixture used in the present invention has usually bitter taste and/or astringent taste and hence they are usually used after modifying the taste by incorporating a conventional sweetening agent as used for foods in the form of granules, compressed products or liquids as mentioned above.

In case of a sold composition, it is further preferably used after coating on the surface of the granules or compressed products. The coating is usually done with a coating agent defined in Japanese Standards of Food Additives, such as methylcellulose (e.g. tradename "Metrose" manufactured by Shin-Etsu Chemical Co., Ltd.), shellac (e.g. tradename "Lac Graze 32E" manufactured by Nippon Shellac Co., Ltd.), soy bean polysaccharide effective for coating of foodstuffs (e.g. hemicellulose manufactured by Fuji Oil Co., Ltd.), or corn protein.

The food of the present invention is usually administered orally 1 to 3 times per day in adult for the purpose of hypotension and/or prevention of cerebral stroke.

When the composition containing a peptide and an electrolyte excretion promoter, e.g. a peptide and chitosan is administered, it shows significantly higher inhibitory effect to rise of blood pressure in comparison with the case of administration of peptide alone and chitosan alone (cf. Experiment 1 disclosed hereinafter). As to alginic acid, the same test was done like in Experiment 1, and it showed significant inhibitory effect to rise of blood pressure by combining a peptide as like as chitosan.

Accordingly, the composition containing a peptide or an electrolyte excretion promoter of the present invention is useful for improvement of lifestyle, reduction of risk factors, and reduction of diseases, those being caused by hypertension.

The present invention will be illustrated in more detail by experiments.

Experiment 1.

Inhibitory Effects on Rise of Blood Pressure in Spontaneous Hypertensive Rat:

(1) Test Samples (Preparation of Samples for Administration to Rats):

a) Sample "a" for Administration to Rats

The composition (40 g) of Example 1 (a composition comprising a peptide crude product 100 g and chitosan (Koyo Chitosan FL-80) 300 g) was homogeneously mixed with powdery feed (960 g) to give Sample "a" for administration to rats.

b) Comparative Sample "b" for Administration to Rats

A peptide crude product (10 g) (corresponding to 0.625 g of C12) was homogeneously mixed with powdery feed (990 g) to give Comparative Sample "b" for administration to rats.

c) Comparative Sample "c" for Administration to Rats

A peptide crude product (30 g) (corresponding to 1.875 g of C12) was homogeneously mixed with powdery feed (970 g) to give Comparative Sample "c" for administration to rats.

d) Comparative Sample "d" for Administration to Rats

A chitosan (Koyo Chitosan FL-80) (30 g) was homogeneously mixed with powdery feed (970 g) to give Comparative Sample "d" for administration to rats.

e) Control Sample "e" for Administration to Rats

Powdery feed per se was used as Control Sample "e" for administration to rats.

(2) Test Method:

Spontaneous hypertensive rats (7 weeks old, hereinafter referred to as "SHR") were used 6 rats in each group. Five groups of rats were previously fed with powdery feed for one week, and thereto each were administered with Sample "a" for administration to rats, Comparative Samples "b" to "d" for administration to rats and Control Sample "e" for administration to rats. Each one week after initiation of feeding, the SHR were subjected to measurement of systolic blood pressure at a tail artery without anesthesia for one month by Tail cuff method.

(3) Test Results:

The average systolic blood pressure at a tail artery when administered with Sample "a" for administration to rats, Comparative Samples "b" to "d" for administration to rats and Control Sample "e" for administration to rats is shown in FIG. 1. During the experiment, the rats in each group were not significantly different between the groups administered with test samples and the group administered with control sample in the amount of ingested sample and in the body weight.

As is clear from FIG. 1, when a composition containing a peptide and an electrolytic excretion promoter was administered, significantly superior inhibitory effects to rise of blood pressure was observed in comparison with the rats administered with peptide alone or chitosan alone.

The present invention is further illustrated by the following Examples.

EXAMPLE 1

A peptide crude product (100 g) (containing 6.25 g of C12 in the mixture) and chitosan (Koyo Chitosan FL-80, manufactured by Koyo Chemical Co., Ltd.) (300 g) were homogeneously mixed to give a composition of Example 1.

EXAMPLE 2

A peptide crude product (100 g) (containing 6.25 g of C12 in the mixture) and alginic acid (Duck Acid, manufactured by Kibun Food Chemifa Co., Ltd.) (300 g) were homogeneously mixed to give a composition of Example 2.

EXAMPLE 3

A peptide crude product (400 g) (containing 25 g of C12 in the mixture), chitosan (Koyo Chitosan FL-80) (250 g), crystalline cellulose (Avicel PH-101, manufactured by Asahi Kasei Corporation) (500 g) and sucrose fatty acid ester (DK Ester F-20W, manufactured by Dai-ichi Kogyo Seiyaku Co., Ltd.) (25 g) were homogeneously mixed. The mixture was subjected to slug tableting (500 mg per tablet) with a rotary tableting machine with a pestle (diameter 15 mm). The resulting tablets were treated with an impact granulation controller to give granulates. The granulates (1000 g) were homogeneously mixed with sucrose fatty acid ester (DK Ester F-20W) (21.3 g), and the mixture was tableted with a rotary tableting machine with a pestle (diameter 8 mm) to give tablets (200 mg per tablet) of Example 3.

EXAMPLE 4

In the same manner as described in Example 3 except that crystalline cellulose (Avicel PH-101) (480 g) and carboxymethylcellulose calcium (ECG-505, manufactured by Gotoku Chemical Co., Ltd.) (20 g) were used instead of crystalline cellulose (Avicel PH-101) (500 g) and that a rotary tableting machine with a pestle (diameter 10 mg) was used to give tablets (400 mg per tablet), there were prepared tablets of Example 4.

EXAMPLE 5

A peptide crude product (400 g) (containing 25 g of C12 in the mixture), chitosan (Koyo Chitosan FL-80) (250 g), crystalline cellulose (Avicel PH-101) (632.5 g) and sucrose fatty acid ester (DK Ester F-20W) (34 g) were homogeneously mixed. The mixture was subjected to slug tableting (500 mg per tablet) with a rotary tableting machine with a pestle (diameter 15 mm). The resulting tablets were treated with an impact granulation controller to give granulates. The granulates (1000 g) were homogeneously mixed with sucrose fatty acid ester (DK Ester F-20W) (25.4 g), and the mixture was tabletted with a rotary tabletting machine with a pestle (diameter 9 mm) to give tablets (300 mg per tablet) of Example 5.

EXAMPLE 6

A peptide crude product (400 g) (containing 25 g of C12 in the mixture), chitosan (Koyo Chitosan FM-80, manufactured by Koyo Chemical Co., Ltd.) (250 g), crystalline cellulose (Avicel PH-101) (557.5 g), sodium hydrogen carbonate (manufactured by Tosoh Corporation) (75 g) and sucrose fatty acid ester (DK Ester F-20W) (34 g) were homogeneously mixed. The mixture was subjected to slug tabletting (500 mg per tablet) with a rotary tabletting machine with a pestle (diameter 15 mm). The resulting tablets were treated with an impact granulation controller to give granules. The granules (1000 g) were homogeneously mixed with sucrose fatty acid ester (DK Ester F-20W) (25.4 g), and the mixture was tabletted with a rotary tabletting machine with a pestle (diameter 9 mm) to give tablets (300 mg per tablet) of Example 6.

EXAMPLE 7

In the same manner as described in Example 6 except that crystalline cellulose (Avicel PH-101) (632.5 g) was used instead of crystalline cellulose (Avicel PH-101) (557.5 g) and sodium hydrogen carbonate (75 g), there were prepared tablets of Example 7.

EXAMPLE 8

A mixture of a peptide crude product (400 g) (containing 25 g of C12 in the mixture), chitosan (Koyo Chitosan FM-80) (250 g) and white sugar (Frost Sugar FS-2, manufactured by Nissin Sugar Manufacturing Co. Ltd.) (537.5 g) was granulated using a 90% aqueous ethanol as a binder with a universal agitator, and dried in a fluidized bed granulator, followed by passing through a 18 mesh sieve to give granules. The granules (940 g) were homogeneously mixed with sucrose fatty acid ester (DK Ester F-20W) (20 g), and the mixture was tabletted with a rotary tabletting machine with a pestle (diameter 8 mm) to give tablets (200 mg per tablet) of Example 8.

EXAMPLE 9

Shellac was dissolved in 95% aqueous ethanol to prepare an aqueous solution containing 10% by weight of shellac, which was used as a coating solution.

The tablets prepared in Example 3 were charged in a pan coating machine, and the above coating solution was sprayed onto the tablets, and the resulting tablets were dried to give film coated tablets of Example 9.

EXAMPLE 10

An aqueous solution containing 8 % by weight of methyl cellulose and 2% by weight of glycerin was used as a coating solution.

The tablets prepared in Example 4 ware charged in a pan coating machine, and the above coating solution was sprayed onto the tablets, and the resulting tablets were dried to give film coated tablets of Example 10.

EXAMPLE 11

A 10% aqueous ethanol solution containing 9% by weight of soy bean polysaccharide and 2% by weight of glycerin was used as a coating solution.

The tablets prepared in Example 5 ware charged in a pan coating machine, and the above coating solution was sprayed onto the tablets, and the resulting tablets were dried to give film coated tablets of Example 11.

EXAMPLE 12

Corn protein was dissolved in 70% aqueous ethanol to prepare an aqueous solution containing 5% by weight of corn protein, which was used as a coating solution.

The tablets prepared in Example 6 ware charged in a pan coating machine, and the above coating solution was sprayed onto the tablets, and the resulting tablets were dried to give film coated tablets of Example 12.

EXAMPLE 13

A peptide crude product (400 g) (containing 25 g of C12 in the mixture), alginic acid (Duck Acid) (250 g), crystalline cellulose (Avicel PH-101) (500 g), and sucrose fatty acid ester (DK Ester F-20W, manufactured by Dai-ichi Kogyo Seiyaku Co. Ltd.) (50 g) were homogeneously mixed. The mixture was subjected to tabletting with a rotary tabletting machine with a pestle (diameter 7 mm) to give tablets (200 mg per tablet) of Example 13.

EXAMPLE 14

A peptide crude product (41 g) (containing 2.5 g of C12 in the mixture), chitosan (Koyo Chitosan FL-80) and an acidifier (50 g) were dissolved in purified water (5 kg) with heating, and thereto were added aspartic acid (manufactured by Tanabe Seiyaku Co., Ltd.) (10 g), a sweetening agent (1.8 g), sugar alcohol (50 g), and further added purified water in an appropriate amount to dissolve them. After cooling, to the mixture was added a flavor (15 g) and further purified water so as to be 10 kg in total. The thus prepared solution was packed in vessels (content, each 200 g) to give a drink of Example 14.

INDUSTRIAL APPLICABILITY

According to the present invention, by combining a low molecular weight peptide or peptide mixture which is obtained by lysing a food-origin protein casein with a protease with an electrolyte excretion promoter selected from one or more of chitosan, alginic acid and a salt thereof, there is a composition or food which exhibits excellent inhibitory activity to rise of blood pressure when administered in human owing to synergistic effects of each components. Accordingly, the composition and food can be used daily for the purpose of keeping the healthy life, particularly for aged persons who tends to show high blood pressure.

The invention claimed is:

1. A composition comprising one or more peptides selected from (a) a peptide having a sequence of Phe-Phe-Val-Ala-Pro-Phe-Pro-Glu-Val-Phe-Gly-Lys (SEQ ID NO: 1), (b) a peptide having a sequence of Ala-Val-Pro-Tyr-Pro-Gln-Arg (SEQ ID NO: 2), and (c) a peptide having a sequence of Thr-Thr-Met-Pro-Leu-Trp (SEQ ID NO: 3), or an acid addition salt thereof, and one or more electrolyte excretion promoters selected from chitosan and alginic acid, the chitosan having an average molecular weight such that it shows a viscosity of not more than 100 mPa·s at 20° C. in a 0.5% aqueous solution.

2. A food a comprising a composition of claim 1.

3. The food according to claim 2, which is in the form of a compressed product.

4. The food according to claim 2, which is in the form of a liquid product.

5. The composition according to claim 1, wherein the electrolyte excretion promoter is chitosan.

6. The composition according to claim 1, wherein the electrolyte excretion promoter is alginic acid.

* * * * *